United States Patent [19]

Wiese et al.

[11] Patent Number: 4,550,620
[45] Date of Patent: Nov. 5, 1985

[54] END-FILLING SAMPLER FOR MOLTEN METALS

[75] Inventors: John R. Wiese, Pittsburgh; Thomas J. Walsh, Butler, both of Pa.

[73] Assignee: General Signal Corporation, Stamford, Conn.

[21] Appl. No.: 555,218

[22] Filed: Nov. 25, 1983

[51] Int. Cl.⁴ .............................................. G01N 1/12
[52] U.S. Cl. .................... 73/864.55; 374/25; 374/157
[58] Field of Search ......... 73/DIG. 9, 864.53, 864.54, 73/864.55, 864.56, 864.57, 864.58, 864.59, 864.63; 374/25, 157

[56] References Cited

U.S. PATENT DOCUMENTS

| | | | |
|---|---|---|---|
| 2,333,711 | 11/1943 | Dwiggins | 73/864.63 |
| 3,460,393 | 8/1969 | Putnam | 73/DIG. 9 |
| 3,501,963 | 3/1970 | Collins | 73/DIG. 9 |
| 3,877,309 | 4/1975 | Hance | 73/864.58 |
| 3,913,404 | 10/1975 | Boron | 73/864.56 |

FOREIGN PATENT DOCUMENTS 532030 10/1976 U.S.S.R. .

Primary Examiner—S. Clement Swisher
Attorney, Agent, or Firm—Harold Huberfeld; Raymond F. MacKay

[57] ABSTRACT

An end-fill molten metal sampler is provided with a ball type check valve within the entrance passageway to the sample cavity.

9 Claims, 3 Drawing Figures

END-FILLING SAMPLER FOR MOLTEN METALS

This invention relates to immersion samplers for molten metal and more particularly to end-fill samplers that are filled through an entrance in the immersion end of the sampler.

BACKGROUND OF THE INVENTION

Obtaining samples of molten metal for laboratory analysis has been a problem confronting metallurgists for many years. Since the introduction of the basic oxygen furnace for the refining of steel with its relatively short refining time, there has been greater emphasis on immersion samplers in which the sample chamber or mold is directly immersed in the molten metal to be sampled.

Commercially available samplers generally fall into one of two categories; side-fill or end-fill. In the side-fill type the molten metal enters the sampler chamber through a passageway located in the sidewall of the sampler at or near the upper end of the sampler chamber when the sampling device is immersed in the molten metal. With such a filling arrangement there is no possibility for the molten metal sample to run out of the sampler chamber even though the sample is still in its liquid state when the sampling device is withdrawn from the bath of molten metal to be sampled.

An end-fill sampling device has its passageway to the sampler chamber located in the immersion end wall of the sampler chamber or in the side wall at or near the immersion end wall. The end-fill sampling device is preferred over the side-fill type by some because the molten metal entering the passageway in the immersion end of the sampling device is considered to be more representative of the molten metal in the bath and less likely to be contaminated by the material used in accomplishing the immersion of the sampling device.

When an end-fill sampler is immersed in a bath of molten metal the metal flows into the sampler chamber through the passageway. Because of the temperature and mass of the sampling device the sample of molten metal begins to cool and solidify in the passageway and sampler chamber and the sampling device may be removed from the molten metal bath with the sample remaining in the sampler chamber.

The end-fill sampling device, however, may experience a loss or run out of the sample upon withdrawal from the bath of molten metal if the metal in the passageway and/or the metal in the bottom end of the sampler chamber has not solidified before the sampling device is withdrawn from the bath of molten metal. This tendency to a run out of the sample is greatest when either the bath of molten metal has a high degree of superheat or the sampler chamber is large or both.

BRIEF DESCRIPTION OF THE INVENTION

The subject invention overcomes the problem of sample run out in an end-fill sampling device by providing in the passageway to the sampler chamber a check valve arrangement that permits the molten metal to flow into the sampler chamber, but prevents flow of molten metal out of the sampler chamber when the sampling device is removed from the bath of molten metal before the metal in the sampler chamber has solidified.

The passageway to the sampler chamber preferably has a circular cross-section that is larger at the sampler chamber end than at the bath end. Located within the passageway is a freely moving ball that is larger in cross sectional area than the bath end of the passageway and smaller than the sampler chamber end of the passageway. The sampler chamber end of the passageway is provided with a restraining device to retain the ball at all times within the passageway. The ball is free to move with the flow of molten metal through the passageway and upon immersion of the sampling device into the bath of molten metal the molten metal flows through the passageway moving the ball to allow the molten metal to flow into the sampler chamber. If the sampling device is removed from the bath of molten metal before the metal in the passageway and the sampler chamber solidifies, the molten metal tending to flow out of the passageway moves the ball to the restricted end of the passageway to provide a valve action to prevent flow of the molten metal from the sampling chamber.

Accordingly, a primary object of this invention is the provision of a molten metal sampling device which includes valve means for closing the passageway from the bath of molten metal to the sampler chamber when the sampling device is withdrawn from the bath of molten metal before the metal in the passageway solidifies.

BRIEF DESCRIPTION OF THE DRAWINGS

The above and other objects and advantages will become apparent from the following description when read in conjunction with the accompanying drawings wherein:

Referring now to FIG. 1 a sampling device 10 is shown mounted in the immersion end of a heat resistant tube 12. The sampling device 10 is secured in the heat resistant tube 12 by a suitable refractory cement 14 such as Sauereisen No. 1 manufactured by the Sauereisen Company. Preferably the sampling device 10 includes a body member 16 and a cap 18. The body member 16 preferably is made of a smooth surface, high density, gas impervious, ceramic material. A preferred ceramic for this body member 16 having the desired characteristics is cordierite which is composed of alumina, magnesia and silica.

The sampling device 10 includes a sampler chamber 20, and an entrance passageway 22 having a circular cross-section located in the immersion end of the body member 16. As shown in FIG. 1, the passageway 22 has at its immersion end a restricted opening 24 which has a reduced diameter relative to the diameter of the main portion of the passageway 22.

In order to prevent the outflow of a molten metal sample through the passageway 22 when the sampling device 10 is withdrawn from a bath of molten metal, there is associated with the passageway 22 a check valve arrangement which in FIG. 1 constitutes a ball 26 having a diameter larger than the diameter of the restricted opening 24 and less than the diameter of the passageway 22. As shown in FIG. 1 the ball 26 is in a passageway closing position seated against the upper periphery of the restricted opening 24. Preferably the ball 26 is made of high density alumina.

Figure 1:
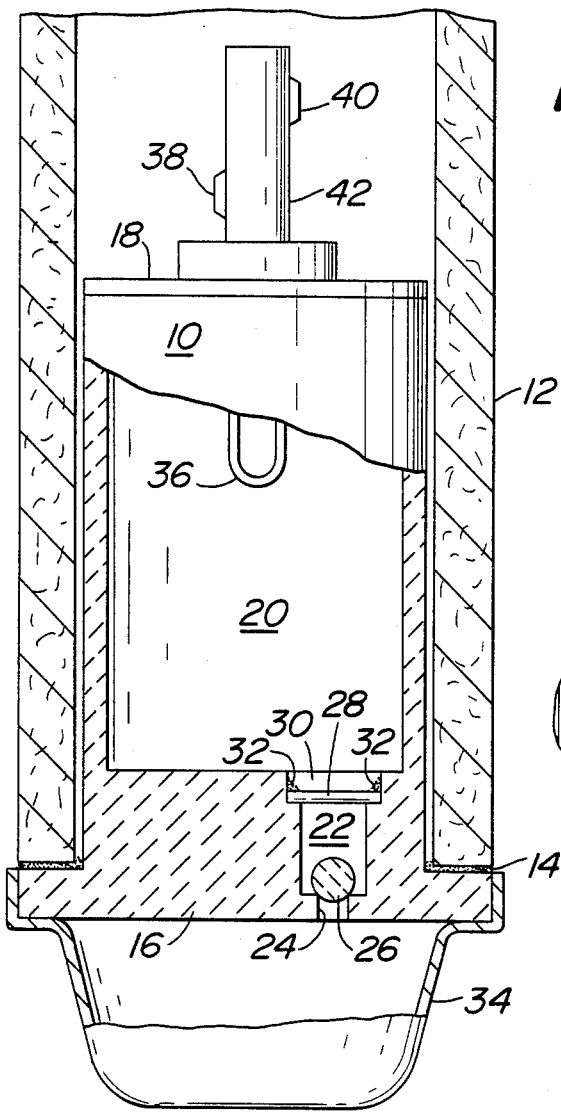
FIG. 1 is a side elevation, partly in cross-section, of a preferred embodiment of a sampling device in accordance with subject invention.

When the sampling device 10 is immersed in a bath of molten metal, the molten metal will tend to flow into the passageway 22 causing the ball 26 to be moved out of its closed position and permit the molten metal to flow into the sampler chamber 20. In order to maintain the ball 26 within the passageway 22 a cross member or bar 28 entends across the passageway 22. In a preferred embodiment the cylindrical passageway 22 terminates in an enlarged opening 30. The cross member 88 is a molybdenum rod diametrically located in the enlarged opening 30 and secured by a suitable refractory cement 32.

If the sampling device 10 is removed from the bath of molten metal before the sample of molten metal in the sampler chamber 20 and passageway 22 is sufficiently solidified, the sample will tend to run out through the passageway 22. Under such conditions the ball 26 will move to the restricted opening 24 to produce a check valve action to stop the flow of the sample out of the sampler chamber 20.

As shown in FIG. 1, the sampler chamber 20 is closed at its upper end by the cap 18 which not only defines the upper end of the sampler chamber 20 but also provides venting means to allow the escape of gases entrapped within the sampler chamber 20 when the sampling device 10 is immersed in a bath of molten metal. In order that the cap 18 may perform its functions it is preferably made of a porous ceramic such as corderite as disclosed in U.S. Pat. No. 3,950,992 issued to R. J. Hance.

Preferably the sampling device 10 is provided with a thin metal cap 34 covering the immersion end of the sampling device 10. The cap 34 insures that when the sampling device is inserted into a bath of molten metal having a layer of slag on its surface that no slag or other surface impurities will enter the passageway 22. Because the cap 34 is made of thin metal the cap 34 will melt or dissolve shortly after the sampling device 10 enters the molten metal. The cap 34 is typically made of cold rolled steel, when the metal being sampled is molten steel.

When the molten metal to be sampled is molten steel the sampler chamber 20 also may include a thermocouple 36 as shown in FIG. 1 for the determination of the carbon content of the molten steel by the thermal arrest method. The electrical leads from the thermocouple 36 pass through the cap 18 and terminate at contacts 38, 40 supported in conventional manner in a tailpiece 42.

Figure 3:
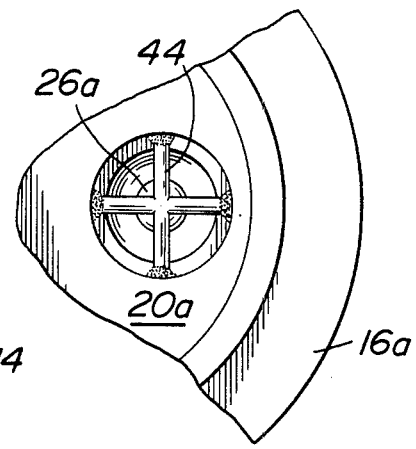
FIG. 3 is a partial plan view of the embodiment shown in FIG. 2
Figure 2:
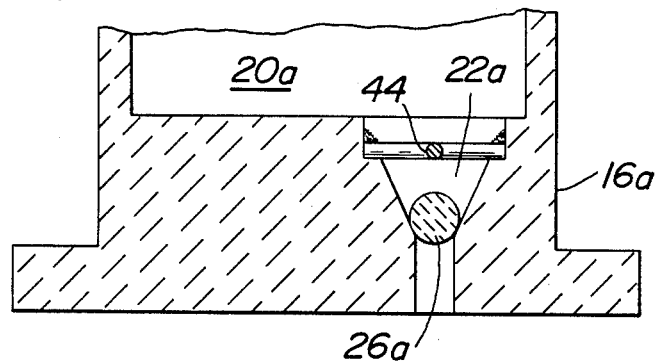
FIG. 2 is a partial side elevation of another embodiment of the invention.

Referring now to FIGS. 2 and 3 there is shown another embodiment of the invention in which the entrance passageway 22a in the body member 16a has sloping sidewalls. In this embodiment as the ball 26a is, upon immersion in a bath of molten metal, moved out of sealing engagement with the sidewall of the passageway 22a by the flow of molten metal the cross sectional flow area will increase as the ball is displaced toward the sampler chamber 20a. Furthermore, the manufacturing tolerances in the dimensions of the passageway 22a and the ball 26a may not be as critical as in the embodiment shown in FIG. 1. In order to prevent the ball 26a from moving out of the passageway 22a and into the sampler chamber 22a a grid 44 is cemented into the end of the passageway 22a.

As is obvious, many different types of check valve arrangements responsive to the direction of flow of the molten metal in the entrance passageway could be used in carrying out the subject invention. Accordingly, reference should be made to the appended claims, rather than to the foregoing specification as indicating the scope of the invention.

What is claimed is:

1. An end-fill immersion sampling device for molten metal comprising
    a sampler chamber for molten metal,
    a passageway through the immersion end of said device for flow of molten metal into said sampler chamber when said device is immersed in molten metal,
    gas vent means at the opposite end of said sampler chamber to permit gas to escape from said sampler chamber when said molten metal is flowing into said sampler chamber, and
    check valve means within said passageway for opening said passageway when said molten metal tends to flow into said sampler chamber and for closing said passageway when said molten metal tends to flow out of said sampler chamber.

2. Apparatus as claimed in claim 1 in which said passageway has a smaller cross section area at its immersion end.

3. Apparatus as claimed in claim 2 in which said check valve means includes a valve member means moveable in said passageway in accordance with flow of said molten metal in said passageway and shaped to seat with said smaller cross section of said passageway to close said passageway when said flow of molten metal is out of said sampler chamber.

4. Apparatus as claimed in claim 3 including restraining means to prevent said valve member means from moving out of said passageway into said sampler chamber when said molten metal is flowing into said sampler chamber.

5. Apparatus as claimed in claim 4 in which said valve member means is a solid high density ball.

6. Apparatus as claimed in claim 5 in which said passageway is cylindrical in shape and said restraining means is a bar across the sampler chamber end of said passageway.

7. Apparatus as claimed in claim 5 in which said passageway is in the shape of a truncated cone with its truncated end at the immersion end of said passageway.

8. An end-fill immersion sampling device for molten metal comprising
    a sampler chamber for molten metal;
    a cylindrical passageway through the immersion end of said device for flow of molten metal into said sampler chamber when said device is immersed in molten metal, said passageway having a smaller cross section area at its immersion end;
    a ball type check valve in said passageway moveable in accordance with flow of said molten metal in said passageway to seat with said smaller cross section of said passageway to close said passageway when said flow of molten metal is out of said sampler chamber;
    a restraining bar across the sampler chamber end of said passageway to prevent said ball from moving out of said passageway when said molten metal is flowing into said sampler chamber; and
    a fusible metal cap covering the immersion end of said passageway.

9. Apparatus as claimed in claim 8 in which said sampler chamber includes a thermocouple for measuring the temperature of the metal in said sampler chamber.

* * * * *